United States Patent [19]
Lin et al.

[11] Patent Number: 5,981,482
[45] Date of Patent: Nov. 9, 1999

[54] INTERLEUKIN-1 RECEPTOR INTRACELLULAR LIGAND PROTEINS

[75] Inventors: Lih-Ling Lin, Concord; James Graham, Somerville, both of Mass.

[73] Assignee: Genetics Institute Inc., Cambridge, Mass.

[21] Appl. No.: 08/726,036

[22] Filed: Oct. 7, 1996

Related U.S. Application Data

[62] Division of application No. 08/487,942, Jun. 7, 1995.

[51] Int. Cl.$^6$ .......................... C07K 14/47; C12N 15/12; C12N 15/63
[52] U.S. Cl. ......................... 514/12; 530/350; 435/69.1; 435/71.1; 435/71.2; 435/172.3; 435/252.3; 435/320.1
[58] Field of Search ............................... 530/350; 514/2, 514/12; 435/69.1, 71.1, 71.2, 172.3, 252.3, 320.1

[56] References Cited

FOREIGN PATENT DOCUMENTS

WO 95/33819  12/1995  WIPO .

OTHER PUBLICATIONS

Sambrook et al. (1989) Molecular Cloning A Laboratory Manual, Cold Spring Harbor Laboratory Press, 2$^{nd}$ edition, pp. 17.2–17.10.

Sorimachi et al. (1990) Biol. Chem. Hoppe–Seylev 371 [Suppl.] pp. 171–176.

Imajoh et al., Biochemistry 27:8122–8128 (1988).

Hillier et al., EMBL Database HS7641, Abstract T69976 (1995).

Hillier et al., EMBL Database HS17371, Abstract T54461 (1995).

Hillier et al., EMBL Database HS26829, Abstract T59268 (1995).

Hillier et al., EMBL Database HS22728, Abstract T59227 (1995).

Hillier et al., EMBL Database HS17371, Abstract T98173 (1995).

Emori et al., The Journal of Biological Chemistry 261(20):9465–9471 (1986).

DeLuca et al., Biochemica et Biophysica Acta 1216:81–93 (1993).

Sorimachi et al., EMBL Database S10590, Abstract XP002015173.

Horuk et al., Biochem Journal 273(1):79–83 (1991).

McKean et al., Journal of Experimental Medicine 180(4):1321–1328 (1994).

PCT International Application No. PCT/US96/06363.

*Primary Examiner*—Prema Mertz
*Attorney, Agent, or Firm*—Scott A. Brown

[57] ABSTRACT

Novel IL-1-R intracellular ligand proteins are disclosed. Polynucleotides encoding the IL-1-R intracellular ligand protein are also disclosed, along with vectors, host cells, and methods of making the IL-1-R intracellular ligand protein. Pharmaceutical compositions containing the IL-1-R intracellular ligand protein, methods of treating inflammatory conditions, and methods of inhibiting IL-1-R intracellular domain binding are also disclosed. Methods of identifying inhibitors of IL-1-R intracellular domain binding and inhibitors identified by such methods are also disclosed.

12 Claims, 2 Drawing Sheets

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 1571 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (ix) FEATURE:
    (A) NAME/KEY: CDS
    (B) LOCATION: 2..529

(xi) SEQUENCE DESCRIPTION: SEQ ID NO:1:

| | | | | | | | | | | | | | | | | |
|---|---|---|---|---|---|---|---|---|---|---|---|---|---|---|---|---|
| G | ATC | CCC | AGG | GTG | GAC | CTC | CGG | GTG | TGG | CAG | GAC | TGC | TGT | GAA | GAC | 46 |
|   | Ile | Pro | Arg | Val | Asp | Leu | Arg | Val | Trp | Gln | Asp | Cys | Cys | Glu | Asp | |
|   | 1 | | | 5 | | | | | 10 | | | | | 15 | | |

```
TGT AGG ACC AGG GGG CAG TTC AAT GCC TTT TCC TAT CAT TTC CGA GGC        94
Cys Arg Thr Arg Gly Gln Phe Asn Ala Phe Ser Tyr His Phe Arg Gly
             20                  25                  30

AGA CGG TCT CTT GAG TTC AGC TAC CAG GAG GAC AAG CCG ACC AAG AAA       142
Arg Arg Ser Leu Glu Phe Ser Tyr Gln Glu Asp Lys Pro Thr Lys Lys
             35                  40                  45

ACA AGA CCA CGG AAA ATA CCC AGT GTT GGG AGA CAG GGG GAA CAT CTC       190
Thr Arg Pro Arg Lys Ile Pro Ser Val Gly Arg Gln Gly Glu His Leu
 50                  55                  60

AGC AAC AGC ACC TCA GCC TTC AGC ACA CGC TCA GAT GCA TCT GGG ACA       238
Ser Asn Ser Thr Ser Ala Phe Ser Thr Arg Ser Asp Ala Ser Gly Thr
 65                  70                  75

AAT GAC TTC AGA GAG TTT GTT CTG GAA ATG CAG AAG ACC ATC ACA GAC       286
Asn Asp Phe Arg Glu Phe Val Leu Glu Met Gln Lys Thr Ile Thr Asp
 80                  85                  90                  95

CTC AGA ACA CAG ATA AAG AAA CTT GAA TCA CGG CTC AGT ACC ACA GAG       334
Leu Arg Thr Gln Ile Lys Lys Leu Glu Ser Arg Leu Ser Thr Thr Glu
                100                 105                 110

TGC GTG GAT GCC GGG GGC GAA TCT CAC GCC AAC AAC ACC AAG TGG AAA       382
Cys Val Asp Ala Gly Gly Glu Ser His Ala Asn Asn Thr Lys Trp Lys
             115                 120                 125

AAA GAT GCA TGC ACC ATT TGT GAA TGC AAA GAC GGG CAG GTC ACC TGC       430
Lys Asp Ala Cys Thr Ile Cys Glu Cys Lys Asp Gly Gln Val Thr Cys
             130                 135                 140

TTC GTG GAA GCT TGC CCC CCT GCC ACC TGT GCT GTC CCC GTG AAC ATC       478
Phe Val Glu Ala Cys Pro Pro Ala Thr Cys Ala Val Pro Val Asn Ile
145                 150                 155

CCA GGG GCC TGC TGT CCA GTC TGC TTA CAG AAG AGG GCG GAG GAA AAG       526
Pro Gly Ala Cys Cys Pro Val Cys Leu Gln Lys Arg Ala Glu Glu Lys
160                 165                 170                 175

CCC TAGGCTCCTG GGAGGCTCCT CAGAGTTTGT CTGCTGTGCC ATCGTGAGAT            579
Pro

CGGGTGGCCG ATGGCAGGGA GCTGCGGACT GCAGACCAGG AAACACCCAG AACTCGTGAC     639

ATTTCATGAC AACGTCCAGC TGGTGCTGTT ACAGAAGGCA GTGCAGGAGG CTTCCAACCA     699

GAGCATCTGC GGAGAAGGAG GCACAGCAGG TGCCTGAAGG GAAGCAGGCA GGAGTCCTAG     759

CTTCACGTTA GACTTCTCAG GTTTTTATTT AATTCTTTTA AAATGAAAAA TTGGTGCTAC     819

TATTAAATTG CACAGTTGAA TCATTTAGGC GCCTAAATTG ATTTTGCCTC CCAACACCAT     879

TTCTTTTTAA ATAAAGCAGG ATACCTCTAT ATGTCAGCCT TGCCTTGTTC AGATGCCAGG     939

AGCCGGCAGA CCTGTCACCC GCAGGTGGGG TGAGTCTCGG AGCTGCCAGA GGGGCTCACC     999

GAAATCGGGG TTCCATCACA AGCTATGTTT AAAAAGAAAA TTGGTGTTTG CCAAACGGAA    1059

CAGAACCTTT GATGAGAGCG TTCACAGGGA CACTGTCTGG GGGTGCAGTG CAAGCCCCCG    1119

GCCTCTTCCC TGGGAACCTC TGAACTCCTC CTTCCTCTGG GCTCTCTGTA ACATTTCACC    1179

ACACGTCAGC ATCTAATCCC AAGACAAACA TTCCCGCTGC TCGAAGCAGC TGTATAGCCT    1239

GTGACTCTCC GTGTGTCAGC TCCTTCCACA CCTGATTAGA ACATTCATAA GCCACATTTA    1299

GAAACAGGTT TGCTTTCAGC TGTCACTTGC ACACATACTG CCTAGTTGTG AACCAAATGT    1359
```

-continued

```
GAAAAAACCT CCTTCATCCC ATTGTGTATC TGATACCTGC CGAGGGCCAA GGGTGTGTGT    1419

TGACAACGCC GCTCCCAGCC GGCCCTGGTT GCGTCCACGT CCTGAACAAG AGCCGCTTCC    1479

GGATGGCTCT TCCCAAGGGA GGAGGAGCTC AAGTGTCGGG AACTGTCTAA CTTCAGGTTG    1539

TGTGAGTGCG TTAAAAAAAA AAAAAAAAA AA                                   1571
```

(2) INFORMATION FOR SEQ ID NO:2:

(i) SEQUENCE CHARACTERISTICS:
        (A) LENGTH: 176 amino acids
        (B) TYPE: amino acid
        (D) TOPOLOGY: linear (ii) MOLECULE TYPE: protein (xi) SEQUENCE DESCRIPTION: SEQ ID NO:2:

```
Ile Pro Arg Val Asp Leu Arg Val Trp Gln Asp Cys Cys Glu Asp Cys
  1               5                  10                  15

Arg Thr Arg Gly Gln Phe Asn Ala Phe Ser Tyr His Phe Arg Gly Arg
                 20                  25                  30

Arg Ser Leu Glu Phe Ser Tyr Gln Glu Asp Lys Pro Thr Lys Lys Thr
             35                  40                  45

Arg Pro Arg Lys Ile Pro Ser Val Gly Arg Gln Gly Glu His Leu Ser
         50                  55                  60

Asn Ser Thr Ser Ala Phe Ser Thr Arg Ser Asp Ala Ser Gly Thr Asn
 65                  70                  75                  80

Asp Phe Arg Glu Phe Val Leu Glu Met Gln Lys Thr Ile Thr Asp Leu
                 85                  90                  95

Arg Thr Gln Ile Lys Lys Leu Glu Ser Arg Leu Ser Thr Thr Glu Cys
                100                 105                 110

Val Asp Ala Gly Gly Glu Ser His Ala Asn Asn Thr Lys Trp Lys Lys
            115                 120                 125

Asp Ala Cys Thr Ile Cys Glu Cys Lys Asp Gly Gln Val Thr Cys Phe
        130                 135                 140

Val Glu Ala Cys Pro Pro Ala Thr Cys Ala Val Pro Val Asn Ile Pro
145                 150                 155                 160

Gly Ala Cys Cys Pro Val Cys Leu Gln Lys Arg Ala Glu Glu Lys Pro
                165                 170                 175
```

(2) INFORMATION FOR SEQ ID NO:3:

(i) SEQUENCE CHARACTERISTICS:
        (A) LENGTH: 1088 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 2..961

(xi) SEQUENCE DESCRIPTION: SEQ ID NO:3:

```
G AAA AAA GGA GGT AAA ACA GAA CAG GAT GGC TAT CAG AAA CCC ACC         46
  Lys Lys Gly Gly Lys Thr Glu Gln Asp Gly Tyr Gln Lys Pro Thr
    1               5                  10                  15

AAC AAA CAC TTC ACG CAG AGT CCC AAG AAG TCA GTG GCC GAC CTG CTG      94
Asn Lys His Phe Thr Gln Ser Pro Lys Lys Ser Val Ala Asp Leu Leu
                 20                  25                  30
```

| | | |
|---|---|---|
| GGG TCC TTT GAA GGC AAA CGA AGA CTC CTT CTG ATC ACT GCT CCC AAG<br>Gly Ser Phe Glu Gly Lys Arg Arg Leu Leu Leu Ile Thr Ala Pro Lys<br>35 40 45 | | 142 |
| GCT GAG AAC AAT ATG TAT GTG CAA CAA CGT GAT GAA TAT CTG GAA AGT<br>Ala Glu Asn Asn Met Tyr Val Gln Gln Arg Asp Glu Tyr Leu Glu Ser<br>50 55 60 | | 190 |
| TTC TGC AAG ATG GCT ACC AGG AAA ATC TCT GTG ATC ACC ATC TTC GGC<br>Phe Cys Lys Met Ala Thr Arg Lys Ile Ser Val Ile Thr Ile Phe Gly<br>65 70 75 | | 238 |
| CCT GTC AAC AAC AGC ACC ATG AAA ATC GAC CAC TTT CAG CTA GAT AAT<br>Pro Val Asn Asn Ser Thr Met Lys Ile Asp His Phe Gln Leu Asp Asn<br>80 85 90 95 | | 286 |
| GAG AAG CCC ATG CGA GTG GTG GAT GAT GAA GAC TTG GTA GAC CAG CGT<br>Glu Lys Pro Met Arg Val Val Asp Asp Glu Asp Leu Val Asp Gln Arg<br>100 105 110 | | 334 |
| CTC ATC AGC GAG CTG AGG AAA GAG TAC GGA ATG ACC TAC AAT GAC TTC<br>Leu Ile Ser Glu Leu Arg Lys Glu Tyr Gly Met Thr Tyr Asn Asp Phe<br>115 120 125 | | 382 |
| TTC ATG GTG CTA ACA GAT GTG GAT CTG AGA GTC AAG CAA TAC TAT GAG<br>Phe Met Val Leu Thr Asp Val Asp Leu Arg Val Lys Gln Tyr Tyr Glu<br>130 135 140 | | 430 |
| GTA CCA ATA ACA ATG AAG TCT GTG TTT GAT CTG ATC GAT ACT TTC CAG<br>Val Pro Ile Thr Met Lys Ser Val Phe Asp Leu Ile Asp Thr Phe Gln<br>145 150 155 | | 478 |
| TCC CGA ATC AAA GAT ATG GAG AAG CAG AAG AAG GAG GGC ATT GTT TGC<br>Ser Arg Ile Lys Asp Met Glu Lys Gln Lys Lys Glu Gly Ile Val Cys<br>160 165 170 175 | | 526 |
| AAA GAG GAA GTT GGG GGA GTG TTA GAA CTG TTC CCA ATT AAT GGG AGC<br>Lys Glu Glu Val Gly Gly Val Leu Glu Leu Phe Pro Ile Asn Gly Ser<br>180 185 190 | | 574 |
| TCT GTT GTT GAG CGA GAA GAC GTA CCA GCC CAT TTG GTG AAA GAC ATT<br>Ser Val Val Glu Arg Glu Asp Val Pro Ala His Leu Val Lys Asp Ile<br>195 200 205 | | 622 |
| CGT AAC TAT TTT CAA GTG AGC CCG GAG TAC TTC TCC ATG CTT CTA GTC<br>Arg Asn Tyr Phe Gln Val Ser Pro Glu Tyr Phe Ser Met Leu Leu Val<br>210 215 220 | | 670 |
| GGA AAA GAC GGA AAT GTC AAA TCC TGG TAT CCT TCC CCA ATG TGG TCC<br>Gly Lys Asp Gly Asn Val Lys Ser Trp Tyr Pro Ser Pro Met Trp Ser<br>225 230 235 | | 718 |
| ATG GTG ATT GTG TAC GAT TTA ATT GAT TCG ATG CAA CTT CGG AGA CAG<br>Met Val Ile Val Tyr Asp Leu Ile Asp Ser Met Gln Leu Arg Arg Gln<br>240 245 250 255 | | 766 |
| GAA ATG GCG ATT CAG CAG TCA CTG GGG ATG CGC TGC CAG AAG ATG AGT<br>Glu Met Ala Ile Gln Gln Ser Leu Gly Met Arg Cys Gln Lys Met Ser<br>260 265 270 | | 814 |
| ATG CAG GCT ATG GTT ACC ATA GTT ACC ACC AAG GAT ACC AGG ATG GTT<br>Met Gln Ala Met Val Thr Ile Val Thr Thr Lys Asp Thr Arg Met Val<br>275 280 285 | | 862 |
| ACC AGG ATG ACT ACC GTC ATC ATG AGA GTT ATC ACC ATG GAT ACC CTT<br>Thr Arg Met Thr Thr Val Ile Met Arg Val Ile Thr Met Asp Thr Leu<br>290 295 300 | | 910 |
| ACT GAG CAG AAA TAT GTA ACC TTA GAC TCA GCC AGT TTC CTC TGC AGC<br>Thr Glu Gln Lys Tyr Val Thr Leu Asp Ser Ala Ser Phe Leu Cys Ser<br>305 310 315 | | 958 |
| TGC TAAAACTACA TGTGGCCAGC TCCATTCTTC CACACTGCGT ACTACATTTC<br>Cys<br>320 | | 1011 |
| CTGCCTTTTT CTTTCAGTGT TTTTCTAAGA CTAAATAAAT AGCAAACTTT CACCTAAAAA | | 1071 |
| AAAAAAAAAA AAAAAA | | 1088 |

-continued (2) INFORMATION FOR SEQ ID NO:4:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO:4:

```
Lys Lys Gly Gly Lys Thr Glu Gln Asp Gly Tyr Gln Lys Pro Thr Asn
  1               5                  10                  15

Lys His Phe Thr Gln Ser Pro Lys Lys Ser Val Ala Asp Leu Leu Gly
             20                  25                  30

Ser Phe Glu Gly Lys Arg Arg Leu Leu Leu Ile Thr Ala Pro Lys Ala
         35                  40                  45

Glu Asn Asn Met Tyr Val Gln Gln Arg Asp Glu Tyr Leu Glu Ser Phe
     50                  55                  60

Cys Lys Met Ala Thr Arg Lys Ile Ser Val Ile Thr Ile Phe Gly Pro
 65                  70                  75                  80

Val Asn Asn Ser Thr Met Lys Ile Asp His Phe Gln Leu Asp Asn Glu
             85                  90                  95

Lys Pro Met Arg Val Val Asp Asp Glu Asp Leu Val Asp Gln Arg Leu
        100                 105                 110

Ile Ser Glu Leu Arg Lys Glu Tyr Gly Met Thr Tyr Asn Asp Phe Phe
        115                 120                 125

Met Val Leu Thr Asp Val Asp Leu Arg Val Lys Gln Tyr Tyr Glu Val
        130                 135                 140

Pro Ile Thr Met Lys Ser Val Phe Asp Leu Ile Asp Thr Phe Gln Ser
145                 150                 155                 160

Arg Ile Lys Asp Met Glu Lys Gln Lys Lys Glu Gly Ile Val Cys Lys
                165                 170                 175

Glu Glu Val Gly Gly Val Leu Glu Leu Phe Pro Ile Asn Gly Ser Ser
                180                 185                 190

Val Val Glu Arg Glu Asp Val Pro Ala His Leu Val Lys Asp Ile Arg
            195                 200                 205

Asn Tyr Phe Gln Val Ser Pro Glu Tyr Phe Ser Met Leu Leu Val Gly
        210                 215                 220

Lys Asp Gly Asn Val Lys Ser Trp Tyr Pro Ser Pro Met Trp Ser Met
225                 230                 235                 240

Val Ile Val Tyr Asp Leu Ile Asp Ser Met Gln Leu Arg Arg Gln Glu
                245                 250                 255

Met Ala Ile Gln Gln Ser Leu Gly Met Arg Cys Gln Lys Met Ser Met
                260                 265                 270

Gln Ala Met Val Thr Ile Val Thr Thr Lys Asp Thr Arg Met Val Thr
            275                 280                 285

Arg Met Thr Thr Val Ile Met Arg Val Ile Thr Met Asp Thr Leu Thr
        290                 295                 300

Glu Gln Lys Tyr Val Thr Leu Asp Ser Ala Ser Phe Leu Cys Ser Cys
305                 310                 315                 320
```

(2) INFORMATION FOR SEQ ID NO:5:

(i) SEQUENCE CHARACTERISTICS:
        (A) LENGTH: 1759 base pairs
        (B) TYPE: nucleic acid
        (C) STRANDEDNESS: double
        (D) TOPOLOGY: linear -continued (ii) MOLECULE TYPE: cDNA (iii) HYPOTHETICAL: NO (ix) FEATURE:
 (A) NAME/KEY: CDS
 (B) LOCATION: 2..754

(xi) SEQUENCE DESCRIPTION: SEQ ID NO:5:

```
C AAA AAC TTC TTC CTG ACG AAT CGC GCC AGG GAG CGC TCA GAC ACC         46
  Lys Asn Phe Phe Leu Thr Asn Arg Ala Arg Glu Arg Ser Asp Thr
  1               5                  10                  15

TTC ATC AAC CTC CGG GAG GTG CTC AAC CGC TTC AAG CTG CCG CCA GGA        94
Phe Ile Asn Leu Arg Glu Val Leu Asn Arg Phe Lys Leu Pro Pro Gly
                20                  25                  30

GAG TAC ATT CTC GTG CCT TCC ACC TTC GAA CCC AAC AAG GAT GGG GAT       142
Glu Tyr Ile Leu Val Pro Ser Thr Phe Glu Pro Asn Lys Asp Gly Asp
            35                  40                  45

TTC TGC ATC CGG GTC TTT TCT GAA AAG AAA GCT GAC TAC CAA GCT GTC       190
Phe Cys Ile Arg Val Phe Ser Glu Lys Lys Ala Asp Tyr Gln Ala Val
        50                  55                  60

GAT GAT GAA ATC GAG GCC AAT CTT GAA GAG TTC GAC ATC AGC GAG GAT       238
Asp Asp Glu Ile Glu Ala Asn Leu Glu Glu Phe Asp Ile Ser Glu Asp
    65                  70                  75

GAC ATT GAT GAT GGA TTC AGG AGA CTG TTT GCC CAG TTG GCA GGA GAG       286
Asp Ile Asp Asp Gly Phe Arg Arg Leu Phe Ala Gln Leu Ala Gly Glu
80                  85                  90                  95

GAT GCG GAG ATC TCT GCC TTT GAG CTG CAG ACC ATC CTG AGA AGG GTT       334
Asp Ala Glu Ile Ser Ala Phe Glu Leu Gln Thr Ile Leu Arg Arg Val
                100                 105                 110

CTA GCA AAG CGC CAA GAT ATC AAG TCA GAT GGC TTC AGC ATC GAG ACA       382
Leu Ala Lys Arg Gln Asp Ile Lys Ser Asp Gly Phe Ser Ile Glu Thr
            115                 120                 125

TGC AAA ATT ATG GTT GAC ATG CTA GAT TCG GAC GGG AGT GGC AAG CTG       430
Cys Lys Ile Met Val Asp Met Leu Asp Ser Asp Gly Ser Gly Lys Leu
        130                 135                 140

GGG CTG AAG GAG TTC TAC ATT CTC TGG ACG AAG ATT CAA AAA TAC CAA       478
Gly Leu Lys Glu Phe Tyr Ile Leu Trp Thr Lys Ile Gln Lys Tyr Gln
145                 150                 155

AAA ATT TAC CGA GAA ATC GAC GTT GAC AGG TCT GGT ACC ATG AAT TCC       526
Lys Ile Tyr Arg Glu Ile Asp Val Asp Arg Ser Gly Thr Met Asn Ser
160                 165                 170                 175

TAT GAA ATG CGG AAG GCA TTA GAA GAA GCA GGT TTC AAG ATG CCC TGT       574
Tyr Glu Met Arg Lys Ala Leu Glu Glu Ala Gly Phe Lys Met Pro Cys
                180                 185                 190

CAA CTC CAC CAA GTC ATC GTT GCT CGG TTT GCA GAT GAC CAG CTC ATC       622
Gln Leu His Gln Val Ile Val Ala Arg Phe Ala Asp Asp Gln Leu Ile
            195                 200                 205

ATC GAT TTT GAT AAT TTT GTT CGG TGT TTG GTT CGG CTG GAA ACG CTA       670
Ile Asp Phe Asp Asn Phe Val Arg Cys Leu Val Arg Leu Glu Thr Leu
        210                 215                 220

TTC AAG ATA TTT AAG CAG CTG GAT CCC GAG AAT ACT GGA ACA ATA GAG       718
Phe Lys Ile Phe Lys Gln Leu Asp Pro Glu Asn Thr Gly Thr Ile Glu
    225                 230                 235

CTC GAC CTT ATC TCT TGG CTC TGT TTC TCA GTA CTT TGAAGTTATA           764
Leu Asp Leu Ile Ser Trp Leu Cys Phe Ser Val Leu
240                 245                 250

ACTAATCTGC CTGAAGACTT CTCATGATGG AAAATCAGCC AAGGACTAAG CTTCCATAGA    824

AATACACTTT GTATCTGGAC CTCAAAATTA TGGGAACATT TACTTAAACG GATGATCATA    884

GCTGAAAATA ATGATACTGT CAATTTGAGA TAGCAGAAGT TTCACACATC AAAGTAAAAG    944
```

```
ATTTGCATAT CATTATACTA AATGCAAATG AGTCGCTTAA CCCTTGACAA GGTCAAAGAA    1004

AGCTTTAAAT CTGTAAATAG TATACACTTT TTACTTTTAC ACACTTTCCT GTTCATAGCA    1064

ATATTAAATC AGGAAAAAAA AATGCAGGGA GGTATTTAAC AGCTGAGCAA AAACATTGAG    1124

TCGCTCTCAA AGGACACGAG GCCCTTGGCA GGGAATATTT AAAGCAACTT CAAGTTTAAA    1184

ATGCAGCTGT TGATTCTACC AAACAACAGT CCAAGATTAC CATTTCCCAT GAGCCAACTG    1244

GGAAACATGG TATATCATGA AGTAATCTTG TCAAGGCATC TGGAGAGTCC AGGAGAGAAG    1304

ACTCACCTCT GTCGCTTGGG TTAAACAAGA GACAGGTTTT GTAGAATATT GATTGGTAAT    1364

AGTAAATCGT TCTCCTTACA ATCAAGTTCT TGACCCTATT CGGCCTTATA CATCTGGTCT    1424

TACAAAGACC AAAGGGATCC TGCGCTTGAT CAACTGAACC AGTATGCCAA ACCAGGCAT     1484

CCAATTTGTA AACCAATTAT GATAAAGGAC AAAATAAGCT GTTTGCCACC TCAAAACTTT    1544

ATGAACTTCA CCACCACTAG TGTCTGTCCA TGGAGTTAGA GGGGACATCA CTTAGAAGTT    1604

CTTATAGAAA GGACACAAGT TTGTTTCCTG GCTTTACCTT GGGAAAATGC TAGCAACATT    1664

ATAGAAATTT TGCCTTGTTG CCTTATCTTC TTCCAAATGT ACTGTTAAAT AAAAATAAAG    1724

GGTTACCCCA TGCAATCAAA AAAAAAAAAA AAAA                                1759
```

(2) INFORMATION FOR SEQ ID NO:6:

(i) SEQUENCE CHARACTERISTICS:
       (A) LENGTH: 251 amino acids
       (B) TYPE: amino acid
       (D) TOPOLOGY: linear (ii) MOLECULE TYPE: protein (xi) SEQUENCE DESCRIPTION: SEQ ID NO:6:

```
Lys Asn Phe Phe Leu Thr Asn Arg Ala Arg Glu Arg Ser Asp Thr Phe
 1               5                  10                  15

Ile Asn Leu Arg Glu Val Leu Asn Arg Phe Lys Leu Pro Pro Gly Glu
             20                  25                  30

Tyr Ile Leu Val Pro Ser Thr Phe Glu Pro Asn Lys Asp Gly Asp Phe
         35                  40                  45

Cys Ile Arg Val Phe Ser Glu Lys Lys Ala Asp Tyr Gln Ala Val Asp
     50                  55                  60

Asp Glu Ile Glu Ala Asn Leu Glu Glu Phe Asp Ile Ser Glu Asp Asp
 65                  70                  75                  80

Ile Asp Asp Gly Phe Arg Arg Leu Phe Ala Gln Leu Ala Gly Glu Asp
                 85                  90                  95

Ala Glu Ile Ser Ala Phe Glu Leu Gln Thr Ile Leu Arg Arg Val Leu
            100                 105                 110

Ala Lys Arg Gln Asp Ile Lys Ser Asp Gly Phe Ser Ile Glu Thr Cys
        115                 120                 125

Lys Ile Met Val Asp Met Leu Asp Ser Asp Gly Ser Gly Lys Leu Gly
    130                 135                 140

Leu Lys Glu Phe Tyr Ile Leu Trp Thr Lys Ile Gln Lys Tyr Gln Lys
145                 150                 155                 160

Ile Tyr Arg Glu Ile Asp Val Asp Arg Ser Gly Thr Met Asn Ser Tyr
                165                 170                 175

Glu Met Arg Lys Ala Leu Glu Glu Ala Gly Phe Lys Met Pro Cys Gln
            180                 185                 190

Leu His Gln Val Ile Val Ala Arg Phe Ala Asp Asp Gln Leu Ile Ile
        195                 200                 205
```

```
Asp Phe Asp Asn Phe Val Arg Cys Leu Val Arg Leu Glu Thr Leu Phe
    210                 215                 220

Lys Ile Phe Lys Gln Leu Asp Pro Glu Asn Thr Gly Thr Ile Glu Leu
225                 230                 235                 240

Asp Leu Ile Ser Trp Leu Cys Phe Ser Val Leu
                245                 250
```

(2) INFORMATION FOR SEQ ID NO:7:

(i) SEQUENCE CHARACTERISTICS:
        (A) LENGTH: 700 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:7:

```
Met Ala Gly Ile Ala Ala Lys Leu Ala Lys Asp Arg Glu Ala Ala Glu
1               5                   10                  15

Gly Leu Gly Ser His Glu Arg Ala Ile Lys Tyr Leu Asn Gln Asp Tyr
                20                  25                  30

Glu Ala Leu Arg Asn Glu Cys Leu Glu Ala Gly Thr Leu Phe Gln Asp
            35                  40                  45

Pro Ser Phe Pro Ala Ile Pro Ser Ala Leu Gly Phe Lys Glu Leu Gly
50                  55                  60

Pro Tyr Ser Ser Lys Thr Arg Gly Met Arg Trp Lys Arg Pro Thr Glu
65                  70                  75                  80

Ile Cys Ala Asp Pro Gln Phe Ile Ile Gly Gly Ala Thr Arg Thr Asp
                85                  90                  95

Ile Cys Gln Gly Ala Leu Gly Asp Cys Trp Leu Leu Ala Ala Ile Ala
                100                 105                 110

Ser Leu Thr Leu Asn Glu Glu Ile Leu Ala Arg Val Val Pro Leu Asn
            115                 120                 125

Gln Ser Phe Gln Glu Asn Tyr Ala Gly Ile Phe His Phe Gln Phe Trp
130                 135                 140

Gln Tyr Gly Glu Trp Val Glu Val Val Asp Asp Arg Leu Pro Thr
145                 150                 155                 160

Lys Asp Gly Glu Leu Leu Phe Val His Ser Ala Glu Gly Ser Glu Phe
                165                 170                 175

Trp Ser Ala Leu Leu Glu Lys Ala Tyr Ala Lys Ile Asn Gly Cys Tyr
                180                 185                 190

Glu Ala Leu Ser Gly Gly Ala Thr Thr Glu Gly Phe Glu Asp Phe Thr
            195                 200                 205

Gly Gly Ile Ala Glu Trp Tyr Glu Leu Lys Lys Pro Pro Pro Asn Leu
210                 215                 220

Phe Lys Ile Ile Gln Lys Ala Leu Gln Lys Gly Ser Leu Leu Gly Cys
225                 230                 235                 240

Ser Ile Asp Ile Thr Ser Ala Ala Asp Ser Glu Ala Ile Thr Phe Gln
                245                 250                 255

Lys Leu Val Lys Gly His Ala Tyr Ser Val Thr Gly Ala Glu Glu Val
                260                 265                 270

Glu Ser Asn Gly Ser Leu Gln Lys Leu Ile Arg Ile Arg Asn Pro Trp
            275                 280                 285

Gly Glu Val Glu Trp Thr Gly Arg Trp Asn Asp Asn Cys Pro Ser Trp
290                 295                 300
```

-continued

```
Asn Thr Ile Asp Pro Glu Glu Arg Glu Arg Leu Thr Arg Arg His Glu
305                 310                 315                 320

Asp Gly Glu Phe Trp Met Ser Phe Ser Asp Phe Leu Arg His Tyr Ser
            325                 330                 335

Arg Leu Glu Ile Cys Asn Leu Thr Pro Asp Thr Leu Thr Ser Asp Thr
                340                 345                 350

Tyr Lys Lys Trp Lys Leu Thr Lys Met Asp Gly Asn Trp Arg Arg Gly
        355                 360                 365

Ser Thr Ala Gly Gly Cys Arg Asn Tyr Pro Asn Thr Phe Trp Met Asn
370                 375                 380

Pro Gln Tyr Leu Ile Lys Leu Glu Glu Glu Asp Glu Asp Glu Glu Asp
385                 390                 395                 400

Gly Glu Ser Gly Cys Thr Phe Leu Val Gly Leu Ile Gln Lys His Arg
                405                 410                 415

Arg Arg Gln Arg Lys Met Gly Asp Met His Thr Ile Gly Phe Gly
            420                 425                 430

Ile Tyr Glu Val Pro Glu Glu Leu Ser Gly Gln Thr Asn Ile His Leu
        435                 440                 445

Ser Lys Asn Phe Phe Leu Thr Asn Arg Ala Arg Glu Arg Ser Asp Thr
450                 455                 460

Phe Ile Asn Leu Arg Glu Val Leu Asn Arg Phe Lys Leu Pro Pro Gly
465                 470                 475                 480

Glu Tyr Ile Leu Val Pro Ser Thr Phe Glu Pro Asn Lys Asp Gly Asp
                485                 490                 495

Phe Cys Ile Arg Val Phe Ser Glu Lys Lys Ala Asp Tyr Gln Ala Val
            500                 505                 510

Asp Asp Glu Ile Glu Ala Asn Leu Glu Glu Phe Asp Ile Ser Glu Asp
        515                 520                 525

Asp Ile Asp Asp Gly Val Arg Arg Leu Phe Ala Gln Leu Ala Gly Glu
    530                 535                 540

Asp Ala Glu Ile Ser Ala Phe Glu Leu Gln Thr Ile Leu Arg Arg Val
545                 550                 555                 560

Leu Ala Lys Arg Gln Asp Ile Lys Ser Asp Gly Phe Ser Ile Glu Thr
                565                 570                 575

Cys Lys Ile Met Val Asp Met Leu Asp Ser Asp Gly Ser Gly Lys Leu
            580                 585                 590

Gly Leu Lys Glu Phe Tyr Ile Leu Trp Thr Lys Ile Gln Lys Tyr Gln
        595                 600                 605

Lys Ile Tyr Arg Glu Ile Asp Val Asp Arg Ser Gly Thr Met Asn Ser
610                 615                 620

Tyr Glu Met Arg Lys Ala Leu Glu Glu Ala Gly Phe Lys Met Pro Cys
625                 630                 635                 640

Gln Leu His Gln Val Ile Val Ala Arg Phe Ala Asp Asp Gln Leu Ile
                645                 650                 655

Ile Asp Phe Asp Asn Phe Val Arg Cys Leu Val Arg Leu Glu Thr Leu
            660                 665                 670

Phe Lys Ile Phe Lys Gln Leu Asp Pro Glu Asn Thr Gly Thr Ile Glu
        675                 680                 685

Leu Asp Leu Ile Ser Trp Leu Cys Phe Ser Val Leu
690                 695                 700
```

INTERLEUKIN-1 RECEPTOR INTRACELLULAR LIGAND PROTEINS

This application is a divisional of application Ser. No. 08/487,942, filed Jun. 7, 1995.

BACKGROUND OF THE INVENTION

The present invention relates to the field of anti-inflammatory substances and other substances which act by inhibiting binding to the intracellular domain of an interleukin-1 receptor (hereinafter "IL-1-R"), such as, for example, the p80, type I IL-1 receptor. More particularly, the present invention is directed to novel ligands which bind to the IL-1-R intracellular domain and to inhibition or modulation of signal transduction by this receptor.

Interleukin-1-α and interleukin-1-β (herein collectively "IL-1") are cytokines which produce a wide range of cellular activities. IL-1 causes an inflammatory response, which can be beneficial, such as in mounting an immune response to a pathogen, or when overexpressed can lead to other detrimental effects of inflammation.

The cellular effects of IL-1 are initiated by the binding of IL-1 to its receptors (IL-1-Rs) on the surface of target cells. The isolation of polynucleotides encoding IL-1-Rs and variant forms of such receptors has been described in U.S. Pat. Nos. 4,968,607, 5,081,228, 5,180,812, in PCT Publication No. WO91/18982, and by Sims et al., PNAS, 86, 8946 (1989) (disclosing the p80, type I IL-1 receptor). Processes for purification of IL-1-Rs have also been disclosed in U.S. Pat. No. 5,296,592.

Native IL-1-Rs are characterized by distinct extracellular, transmembrane and intracellular domains. The primary purpose of the extracellular domain is to present a binding site for IL-1 on the outside of the cell. When IL-1 is bound to the binding site, a "signal" is transmitted to the inside of the cell through the transmembrane and intracellular domains, indicating that binding has occurred. Transmission or "transduction" of the signal to the inside of the cell occurs by a change in conformation of the transmembrane and/or intracellular domains of the receptor. This signal is "received" by the binding of proteins and other molecules to the intracellular domain of the receptor, resulting in the effects seen upon IL-1 stimulation.

While IL-1 binding by IL-1-Rs results in beneficial cellular effects, it is often desirable to prevent or deter IL-1 binding from causing other detrimental cellular effects. Although substantial effort has been expended investigating inhibition of IL-1 binding to the extracellular domain of IL-1-Rs, examination of binding of proteins and other molecules to the intracellular domain of IL-1-Rs has received much less attention.

However, ligands which bind to the IL-1-R intracellular domain have yet to be identified. It would be desirable to identify and isolate such ligands to examine their effects upon IL-1-R signal transduction and their use as therapeutic agents for treatment of IL-1-induced conditions. Furthermore, identification of such ligands would provide a means for screening for inhibitors of IL-1-R/intracellular ligand binding, which will also be useful as anti-inflammatory agents.

SUMMARY OF THE INVENTION

Applicants have for the first time identified novel IL-1-R intracellular ligand proteins and have isolated polynucleotides encoding such ligands. Applicants have also identified certain known proteins which may also bind to the intracellular domain of IL-1-R.

In one embodiment, the present invention provides a composition comprising an isolated polynucleotide encoding a protein having IL-1-R intracellular ligand protein activity. In preferred embodiments, the polynucleotide is selected from the group consisting of:

(a) a polynucleotide comprising the nucleotide sequence of SEQ ID NO:1 from nucleotide 2 to nucleotide 529;

(b) a polynucleotide comprising a fragment of the nucleotide sequence of SEQ ID NO:1, which encodes a protein having IL-1-R intracellular ligand protein activity;

(c) a polynucleotide encoding an IL-1-R intracellular ligand protein comprising the amino acid sequence of SEQ ID NO:2;

(d) a polynucleotide encoding an IL-1-R intracellular ligand protein comprising a fragment of the amino acid sequence of SEQ ID NO:2 and having IL-1-R intracellular ligand protein activity;

(e) a polynucleotide comprising the nucleotide sequence of SEQ ID NO:3 from nucleotide 2 to nucleotide 961;

(f) a polynucleotide comprising a fragment of the nucleotide sequence of SEQ ID NO:3, which encodes a protein having IL-1-R intracellular ligand protein activity;

(g) a polynucleotide encoding an IL-1-R intracellular ligand protein comprising the amino acid sequence of SEQ ID NO:4;

(h) a polynucleotide encoding an IL-1-R intracellular ligand protein comprising a fragment of the amino acid sequence of SEQ ID NO:4 and having IL-1-R intracellular ligand protein activity;

(i) a polynucleotide comprising the nucleotide sequence of SEQ ID NO:5 from nucleotide 2 to nucleotide 754;

(j) a polynucleotide comprising a fragment of the nucleotide sequence of SEQ ID NO:5, which encodes a protein having IL-1-R intracellular ligand protein activity;

(k) a polynucleotide encoding an IL-1-R intracellular ligand protein comprising the amino acid sequence of SEQ ID NO:6;

(l) a polynucleotide encoding an IL-1-R intracellular ligand protein comprising a fragment of the amino acid sequence of SEQ ID NO:6 and having IL-1-R intracellular ligand protein activity; and (m) a polynucleotide capable of hybridizing under stringent conditions to any one of the polynucleotides specified in (a)–(l), which encodes a protein having IL-1-R intracellular ligand protein activity.

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing an IL-1-R intracellular ligand protein, which comprises:

(a) growing a culture of the host cell transformed with such polynucleotide compositions in a suitable culture medium; and (b) purifying the IL-1-R intracellular ligand protein from the culture.

The ligand protein produced according to such methods is also provided by the present invention.

Compositions comprising a protein having IL-1-R intracellular ligand protein activity are also disclosed. In preferred embodiments the protein comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6; and (f) fragments of the amino acid sequence of SEQ ID NO:6;

the protein being substantially free from other mammalian proteins. Such compositions may further comprise a pharmaceutically acceptable carrier.

Compositions comprising an antibody which specifically reacts with such IL-1-R intracellular ligand protein are also provided by the present invention.

Methods are also provided for identifying an inhibitor of IL-1-R intracellular domain binding which comprise:

(a) combining an IL-1-R intracellular domain protein with an IL-1-R intracellular ligand protein, said combination forming a first binding mixture;

(b) measuring the amount of binding between the IL-1-R intracellular domain protein and the IL-1-R intracellular ligand protein in the first binding mixture;

(c) combining a compound with the IL-1-R intracellular domain protein and an IL-1-R intracellular ligand protein to form a second binding mixture;

(d) measuring the amount of binding in the second binding mixture; and (e) comparing the amount of binding in the first binding mixture with the amount of binding in the second binding mixture;

wherein the compound is capable of inhibiting IL-1-R intracellular domain binding when a decrease in the amount of binding of the second binding mixture occurs. In certain preferred embodiments the IL-1-R intracellular ligand protein used in such method comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the amino acid sequence of SEQ ID NO:7; and (h) fragments of the amino acid sequence of SEQ ID NO:7.

Compositions comprising inhibitors identified according to such method are also provided. Such compositions may include pharmaceutically acceptable carriers.

Methods are also provided for preventing or ameliorating an inflammatory condition which comprises administering a therapeutically effective amount of a composition comprising a protein having IL-1-R intracellular ligand protein activity and a pharmaceutically acceptable carrier.

Other embodiments provide methods of inhibiting IL-1-R intracellular domain binding comprising administering a therapeutically effective amount of a composition comprising a protein having IL-1-R intracellular ligand protein activity and a pharmaceutically acceptable carrier.

Methods of preventing or ameliorating an inflammatory condition or of inhibiting IL-1-R intracellular domain binding are provided, which comprise administering to a mammalian subject a therapeutically effective amount of inhibitors of IL-1-R intracellular domain binding, are also provided.

Methods of identifying an inhibitor of IL-1-R intracellular domain binding are also provided by the present invention which comprise:

(a) transforming a cell with a first polynucleotide encoding an IL-1-R intracellular domain protein, a second polynucleotide encoding an IL-1-R intracellular ligand protein, and at least one reporter gene, wherein the expression of the reporter gene is regulated by the binding of the IL-1-R intracellular ligand protein encoded by the second polynucleotide to the IL-1-R intracellular domain protein encoded by the first polynucleotide;

(b) growing the cell in the presence of and in the absence of a compound; and (c) comparing the degree of expression of the reporter gene in the presence of and in the absence of the compound;

wherein the compound is capable of inhibiting IL-1-R intracellular domain binding when a decrease in the degree of expression of the reporter gene occurs. In preferred embodiments, the cell is a yeast cell and the second polynucleotide is selected from the group consisting of:

(a) a polynucleotide comprising the nucleotide sequence of SEQ ID NO:1 from nucleotide 2 to nucleotide 529;

(b) a polynucleotide comprising a fragment of the nucleotide sequence of SEQ ID NO:1, which encodes a protein having IL-1-R intracellular ligand protein activity;

(c) a polynucleotide encoding an IL-1-R intracellular ligand protein comprising the amino acid sequence of SEQ ID NO:2;

(d) a polynucleotide encoding an IL-1-R intracellular ligand protein comprising a fragment of the amino acid sequence of SEQ ID NO:2 and having IL-1-R intracellular ligand protein activity;

(e) a polynucleotide comprising the nucleotide sequence of SEQ ID NO:3 from nucleotide 2 to nucleotide 961;

(f) a polynucleotide comprising a fragment of the nucleotide sequence of SEQ ID NO:3, which encodes a protein having IL-1-R intracellular ligand protein activity;

(g) a polynucleotide encoding an IL-1-R intracellular ligand protein comprising the amino acid sequence of SEQ ID NO:4;

(h) a polynucleotide encoding an IL-1-R intracellular ligand protein comprising a fragment of the amino acid sequence of SEQ ID NO:4 and having IL-1-R intracellular ligand protein activity;

(i) a polynucleotide comprising the nucleotide sequence of SEQ ID NO:5 from nucleotide 2 to nucleotide 754;

(j) a polynucleotide comprising a fragment of the nucleotide sequence of SEQ ID NO:5, which encodes a protein having IL-1-R intracellular ligand protein activity;

(k) a polynucleotide encoding an IL-1-R intracellular ligand protein comprising the amino acid sequence of SEQ ID NO:6;

(l) a polynucleotide encoding an IL-1-R intracellular ligand protein comprising a fragment of the amino acid sequence of SEQ ID NO:6 and having IL-1-R intracellular ligand protein activity;

(m) a polynucleotide encoding an IL-1-R intracellular ligand protein comprising the amino acid sequence of SEQ ID NO:7;

(n) a polynucleotide encoding an IL-1-R intracellular ligand protein comprising a fragment of the amino acid sequence of SEQ ID NO:7 and having IL-1-R intracellular ligand protein activity; and (o) a polynucleotide capable of hybridizing under stringent conditions to any one of the polynucleotides specified in (a)–(n), which encodes a protein having IL-1-R intracellular ligand protein activity.

DETAILED DESCRIPTION OF THE INVENTION

Figure 1:
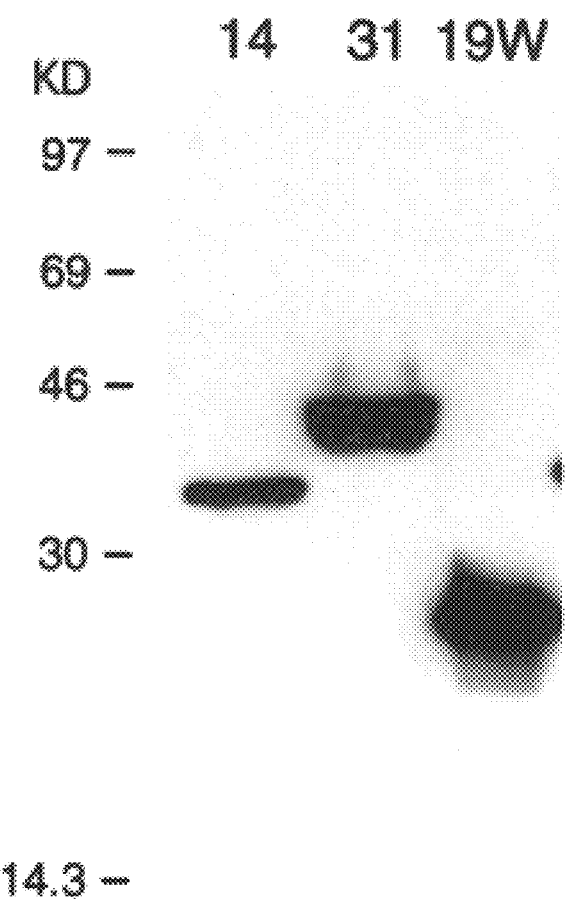
FIG. 1 depicts an autoradiograph demonstrating the expression of IL-1-R intracellular ligand proteins of the present invention in mammalian cells. The expression of flag-14w, -31w and -19w was detected by an anti-flag antibody, M2, as described below.

The present inventors have for the first time identified and isolated novel polynucleotides which encode proteins which bind to the IL-1-R intracellular domain. As used herein "IL-1-R" includes all receptors for interleukin-1. The type I, p80 IL-1-R is the preferred receptor for practicing the present invention.

The sequence of a polynucleotide encoding one such protein is set forth in SEQ ID NO:1 from nucleotide 2 to 529. This polynucleotide has been identified as "clone 19w." The amino acid sequence of the IL-1-R intracellular ligand protein encoded by clone 19w is set forth in SEQ ID NO:2. It is believed that clone 19w is a partial cDNA clone of a longer full length coding sequence. However, as demonstrated herein the protein encoded by clone 19w does bind the intracellular domain of IL-1-R (i.e., has "IL-1-R intracellular ligand protein activity" as defined herein). Clone 19w was deposited with the American Type Culture Collection on Mar. 31, 1995 and given the accession number ATCC 69774. The protein encoded by clone 19w is 176 amino acids in length. No identical or closely related sequences were found using database searches. Therefore, clone 19w encodes a novel protein. However, using an extensive FASTA search, a significant homology to amino acids 330 to 390 of thrombospondin (41% identity in 59 amino acids) is found in the C-terminal portion of the 19w protein. Moreover, a significant homology to the $Ca^{2+}$ binding domain, EF hand of calmodulin (25% in 65 amino acids) is observed in the region between amino acids 40 and 110 of the protein encoded by clone 19w.

The sequence of a polynucleotide encoding another such protein is set forth in SEQ ID NO:3 from nucleotide 2 to 961. This polynucleotide has been identified as "clone 31w." The amino acid sequence of the IL-1-R intracellular ligand protein encoded by clone 31w is set forth in SEQ ID NO:4. It is believed that clone 31w is a partial cDNA clone of a longer full length coding sequence. However, as demonstrated herein the protein encoded by clone 31w does bind the intracellular domain of IL-1-R (i.e., has "IL-1-R intracellular ligand protein activity" as defined herein). Clone 31w was deposited with the American Type Culture Collection on Mar. 31, 1995 and given the accession number ATCC 69775. The protein encoded by clone 31 w is 320 amino acids in length. No identical or closely related sequences were found using BLASTN/BLASTX or FASTA searches. Therefore, clone 31w encodes a novel protein.

The sequence of a polynucleotide encoding another such protein is set forth in SEQ ID NO:5 from nucleotides 2 to 754. This polynucleotide has been identified as "clone 14w." The amino acid sequence of the IL-1-R intracellular ligand protein encoded by clone 14w is set forth in SEQ ID NO:6. It is believed that clone 14w is a partial cDNA clone of a longer full length coding sequence. However, as demonstrated herein the protein encoded by clone 14w does bind the intracellular domain of IL-1-R (i.e., has "IL-1-R intracellular ligand protein activity" as defined herein). CLone 14w was deposited with the American Type Culture Collection on Mar. 31, 1995 and given the accession number ATCC 69773.

The protein encoded by clone 14w is identical to the sequence of amino acids 449 to 700 of calcium activated neutral protease (CANP), with the exception of an amino acid change (Val to Phe) at position 553 of CANP. The sequence of CANP is disclosed in Imajoh et al., Biochemistry 1988, 27, 8122–8128, which is incorporated herein by reference (accession no. A31218). The amino acid sequence of CANP is set forth in SEQ ID NO:7. Based upon this sequence homology, CANP and certain fragments thereof will exhibit IL-1-R intracellular ligand binding activity (as defined herein).

For the purposes of the present application, "IL-1-R intracellular ligand protein" includes proteins which exhibit IL-1-R intracellular ligand protein activity. For the purposes of the present application, a protein is defined as having "IL-1-R intracellular ligand protein activity" when it binds to a protein derived from the IL-1-R intracellular domain. Activity can be measured by using any assay which will detect binding to an IL-1-R intracellular domain protein. Examples of such assays include without limitation the interaction trap assays and assays in which IL-1-R intracellular domain protein which is affixed to a surface in a manner conducive to observing binding, including without limitation those described in Examples 1 and 3. As used herein an "IL-1-R intracellular domain protein" includes the entire intracellular domain or fragments thereof.

Fragments of the IL-1-R intracellular ligand protein which are capable of interacting with the IL-1-R intracellular domain or which are capable of inhibiting IL-1-R intracellular domain binding (i.e., exhibit IL-1-R intracellular ligand protein activity) are also encompassed by the present invention. Fragments of the IL-1-R intracellular ligand protein may be in linear form or they may be cyclized using known methods, for example, as described in H. U. Saragovi, et al; Bio/technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of IL-1-R intracellular ligand protein binding sites. For example, fragments of the IL-1-R intracellular ligand protein may be fused through "linker" sequences to the Fc portion of an immunoglobulin. For a bivalent form of the IL-1-R intracellular ligand protein, such a fusion could be to the Fc portion of an IgG molecule. Other immunoglobulin isotypes may also be used to generate such fusions. For example, an IL-1-R intracellular ligand protein—IgM fusion would generate a decavalent form of the IL-1-R intracellular ligand protein of the invention.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the IL-1-R intracellular ligand protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and the expression control sequence are situated within a vector or cell in such a way that the IL-1-R intracellular ligand protein is expressed by a host cell which has been transformed (transfected) with the ligated polynucleotide/expression control sequence.

A number of types of cells may act as suitable host cells for expression of the IL-1-R intracellular ligand protein. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

The IL-1-R intracellular ligand protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference.

Alternatively, it may be possible to produce the IL-1-R intracellular ligand protein in lower eukaryotes such as yeast or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the IL-1-R intracellular ligand protein is made in yeast or bacteria, it may be necessary to modify the protein produced therein, for example by phosphorylation or glycosylation of the appropriate sites, in order to obtain the functional IL-1-R intracellular ligand protein. Such covalent attachments may be accomplished using known chemical or enzymatic methods.

The IL-1-R intracellular ligand protein of the invention may also be expressed as a product of transgenic animals, e.g., as a component of the milk of transgenic cows, goats, pigs, or sheep which are characterized by somatic or germ cells containing a nucleotide sequence encoding the IL-1-R intracellular ligand protein.

The IL-1-R intracellular ligand protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the IL-1-R intracellular ligand protein may also include an affinity column containing the IL-1-R intracellular domain or other IL-1-R intracellular domain protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the IL-1-R intracellular ligand protein of the invention may also be expressed in a form which will facilitate purification. For example, it may be expressed as a fusion protein, such as those of maltose binding protein (MBP) or glutathione-S-transferase (GST). Kits for expression and purification of such fusion proteins are commercially available from New England BioLab (Beverly, MA) and Pharmacia (Piscataway, N.J.), respectively. The IL-1-R ligand protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the IL-1-R intracellular ligand protein. Some or all of the foregoing purification steps, in various combinations, can also be employed to provide a substantially homogeneous isolated recombinant protein. The IL-1-R intracellular ligand protein thus purified is substantially free of other mammalian proteins and is defined in accordance with the present invention as an "isolated IL-1-R intracellular ligand protein."

IL-1-R intracellular ligand proteins may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with IL-1-R intracellular ligand proteins may possess biological properties in common therewith, including IL-1-R intracellular ligand protein activity. Thus, they may be employed as biologically active or immunological substitutes for natural, purified IL-1-R intracellular ligand proteins in screening of therapeutic compounds and in immunological processes for the development of antibodies.

The IL-1-R intracellular ligand proteins provided herein also include proteins characterized by amino acid sequences similar to those of purified IL-1-R intracellular ligand proteins but into which modification are naturally provided or deliberately engineered. For example, modifications in the peptide or DNA sequences can be made by those skilled in the art using known techniques. Modifications of interest in the IL-1-R intracellular ligand protein sequences may include the replacement, insertion or deletion of a selected amino acid residue in the coding sequence. For example, one or more of the cysteine residues may be deleted or replaced with another amino acid to alter the conformation of the molecule. Mutagenic techniques for such replacement, insertion or deletion are well known to those skilled in the art (see, e.g., U.S. Pat. No. 4,518,584).

Other fragments and derivatives of the sequences of IL-1-R intracellular ligand proteins which would be expected to retain IL-1-R intracellular ligand protein activity in whole or in part and may thus be useful for screening or other immunological methodologies may also be easily made by those skilled in the art given the disclosures herein. Such modifications are believed to be encompassed by the present invention.

IL-1-R intracellular ligand protein of the invention may also be used to screen for agents which are capable of inhibiting or blocking binding of an IL-1-R intracellular ligand protein to the intracellular domain of IL-1-R, and thus may act as inhibitors of IL-1-R intracellular domain binding and/or IL-1 activity. Binding assays using a desired binding protein, immobilized or not, are well known in the art and may be used for this purpose using the IL-1-R intracellular ligand protein of the invention. Examples 1 and 3 describe examples of such assays. Appropriate screening assays may be cell-based or cell-free. Alternatively, purified protein based screening assays may be used to identify such agents. For example, IL-1-R intracellular ligand protein may be immobilized in purified form on a carrier and binding to purified IL-1-R intracellular domain may be measured in the presence and in the absence of potential inhibiting agents. A suitable binding assay may alternatively employ purified IL-1-R intracellular domain immobilized on a carrier, with a soluble form of a IL-1-R intracellular ligand protein of the invention. Any IL-1-R intracellular ligand protein may be used in the screening assays described above.

In such a screening assay, a first binding mixture is formed by combining IL-1-R intracellular domain protein and IL-1-R intracellular ligand protein, and the amount of binding in the first binding mixture ($B_o$) is measured. A second binding mixture is also formed by combining IL-1-R intracellular domain protein. IL-1-R intracellular ligand protein, and the compound or agent to be screened, and the amount of binding in the second binding mixture (B) is measured. The amounts of binding in the first and second binding mixtures are compared, for example, by performing a $B/B_o$ calculation. A compound or agent is considered to be capable of inhibiting IL-1-R intracellular domain binding if a decrease in binding in the second binding mixture as compared to the first binding mixture is observed. The formulation and optimization of binding mixtures is within the level of skill in the art. Such binding mixtures may also contain buffers and salts necessary to enhance or to optimize binding, and additional control assays may be included in the screening assay of the invention.

Alternatively, appropriate screening assays may be cell based. For example, the binding or interaction between an IL-1-R ligand protein and the IL-1-R intracellular domain can be measured in yeast as described below in Examples 1 and 3.

Compounds found to reduce, preferably by at least about 10% more preferably greater than about 50% or more, the binding activity of IL-1-R intracellular ligand protein to IL-1-R intracellular domain may thus be identified and then secondarily screened in other binding assays, including in vivo assays. By these means compounds having inhibitory activity for IL-1-R intracellular domain binding which may be suitable as anti-inflammatory agents may be identified.

Isolated IL-1-R intracellular ligand protein may be useful in treating, preventing or ameliorating inflammatory conditions and other conditions such as osteoporosis, colitis, myelogenous leukemia, diabetes, wasting and atherosclerosis. Isolated IL-1-R intracellular ligand protein may be used itself as an inhibitor of IL-1-R intracellular domain binding or to design inhibitors of IL-1-R intracellular domain binding. Inhibitors of binding of IL-1-R intracellular ligand protein to the IL-1-R intracellular domain ("IL-1-R intracellular binding inhibitors") are also useful for treating such conditions.

The present invention encompasses both pharmaceutical compositions and therapeutic methods of treatment or use which employ isolated IL-1-R intracellular ligand protein and/or binding inhibitors of IL-1-R intracellular binding.

Isolated IL-1-R intracellular ligand protein or binding inhibitors (from whatever source derived, including without limitation from recombinant and non-recombinant cell lines) may be used in a pharmaceutical composition when combined with a pharmaceutically acceptable carrier. Such a composition may also contain (in addition to IL-1-R intracellular ligand protein or binding inhibitor and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, G-CSF, Meg-CSF, stem cell factor, and erythropoietin. The pharmaceutical composition may further contain other anti-inflammatory agents. Such additional factors and/or agents may be included in the pharmaceutical composition to produce a synergistic effect with isolated IL-1-R intracellular ligand protein or binding inhibitor, or to minimize side effects caused by the isolated IL-1-R intracellular ligand protein or binding inhibitor. Conversely, isolated IL-1-R intracellular ligand protein or binding inhibitor may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated IL-1-R intracellular ligand protein or binding inhibitor is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing prevention or amelioration of an inflammatory response or condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated IL-1-R intracellular ligand protein or binding inhibitor is administered to a mammal having a condition to be treated. Isolated IL-1-R intracellular ligand protein or binding inhibitor may be administered in accordance with the method of the invention either alone or in combination with other therapies such as treatments employing cytokines, lymphokines or other hematopoietic factors. When co-administered with one or more cytokines, lymphokines or other hematopoietic factors, isolated IL-1-R intracellular ligand protein or binding inhibitor may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering isolated IL-1-R intracellular ligand protein or binding inhibitor in combination with cytokine(s), lymphokine(s), other hematopoietic factor (s), thrombolytic or anti-thrombotic factors.

Administration of isolated IL-1-R intracellular ligand protein or binding inhibitor used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of isolated IL-1-R intracellular ligand protein or binding inhibitor is administered orally, isolated IL-1-R intracellular ligand protein or binding inhibitor will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% isolated IL-1-R intracellular ligand protein or binding inhibitor, and preferably from about 25 to 90% isolated IL-1-R intracellular ligand protein or binding inhibitor. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of isolated IL-1-R intracellular ligand protein or binding inhibitor, and preferably from about 1 to 50% isolated IL-1-R intracellular ligand protein or binding inhibitor.

When a therapeutically effective amount of isolated IL-1-R intracellular ligand protein or binding inhibitor is administered by intravenous, cutaneous or subcutaneous injection, isolated IL-1-R intracellular ligand protein or binding inhibitor will be in the form of a pyrogen-free parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to isolated IL-1-R intracellular ligand protein or binding inhibitor, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of isolated IL-1-R intracellular ligand protein or binding inhibitor in the pharmaceutical composition of the present invention will depend upon the nature and severity of the condition being treated, and on the nature of prior treatments which the patient has undergone. Ultimately, the attending physician will decide the amount of isolated IL-1-R intracellular ligand protein or binding inhibitor with which to treat each individual patient. Initially, the attending physician will administer low doses of isolated IL-1-R intracellular ligand protein or binding inhibitor and observe the patient's response. Larger doses of isolated IL-1-R intracellular ligand protein or binding inhibitor may be administered until the optimal therapeutic effect is obtained for the patient, and at that point the dosage is not increased further. It is contemplated that the various pharmaceutical compositions used to practice the method of the present invention should contain about 0.1 $\mu$g to about 100 mg of isolated IL-1-R intracellular ligand protein or binding inhibitor per kg body weight.

The duration of intravenous therapy using the pharmaceutical composition of the present invention will vary, depending on the severity of the disease being treated and the condition and potential idiosyncratic response of each individual patient. It is contemplated that the duration of each application of the isolated IL-1-R intracellular ligand protein or binding inhibitor will be in the range of 12 to 24 hours of continuous intravenous administration. Ultimately the attending physician will decide on the appropriate duration of intravenous therapy using the pharmaceutical composition of the present invention.

Isolated IL-1-R intracellular ligand protein of the invention may also be used to immunize animals to obtain polyclonal and monoclonal antibodies which specifically react with the IL-1-R intracellular ligand protein and which may inhibit IL-1-R intracellular domain binding. Such antibodies may be obtained using either the entire IL-1-R intracellular ligand protein or fragments of IL-1-R intracellular ligand protein as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer.Chem.Soc. 85, 2149–2154 (1963); J. L. Krstenansky, et al., FEBS Lett. 211, 10 (1987).

Monoclonal antibodies binding to IL-1-R intracellular ligand protein or to complex carbohydrate moieties characteristic of the IL-1-R intracellular ligand glycoprotein may be useful diagnostic agents for the immunodetection of IL-1-R ligand protein.

Neutralizing monoclonal antibodies binding to IL-1-R intracellular ligand protein or to complex carbohydrates characteristic of IL-1-R intracellular ligand glycoprotein may also be useful therapeutics for both inflammatory conditions and also in the treatment of some forms of cancer where abnormal expression of IL-1-R intracellular ligand protein is involved. These neutralizing monoclonal antibodies are capable of blocking the signaling function of the IL-1-R intracellular ligand protein. By blocking the binding of IL-1-R intracellular ligand protein, certain biological responses to IL-1 are either abolished or markedly reduced. In the case of cancerous cells or leukemic cells, neutralizing monoclonal antibodies against IL-1-R intracellular ligand protein may be useful in detecting and preventing the metastatic spread of the cancerous cells, which may be mediated by the IL-1-R intracellular ligand protein.

Due to the similarity of its sequence to SEQ ID NO:6, CANP and fragments thereof which bind to the IL-1-R intracellular domain are proteins having IL-1-R intracellular ligand protein activity as defined herein. As a result, they are also useful in pharmaceutical compositions, for treating inflammatory conditions and for inhibiting IL-1-R intracellular domain binding as described above for IL-1-R intracellular ligand proteins generally.

EXAMPLE 1

CLONING OF IL-1-R INTRACELLULAR LIGAND PROTEIN ENCODING POLYNUCLEOTIDE

A yeast genetic selection method, the "interaction trap" [Gyuris et al, Cell 75:791–803, 1993, which is incorporated herein by reference], was used to screen WI38 and HeLa cell cDNA libraries (preparation see below) for proteins that interact with IL-1-R-1c, the cytoplasmic portion (intracellular domain) of the interleukin-1 receptor p80, or type I. The IL-1-R-1c DNA, encoding amino acids 340 to 552 of the type I IL-1 receptor, was obtained via the polymerase chain reaction (PCR) of a human WI38 cell cDNA library. This IL-1-R-1c DNA was then cloned into pEG202 by an EcoRI site, generating the bait plasmid, pEG202-IL-1-R-1c. This plasmid contains the HIS3 selectable marker, and expression of the bait, the LexA-IL-1-R-1c fusion protein, is from the strong constitutive ADH1 promoter. To create the reporter strain carrying the bait protein, yeast strain EGY48, containing the reporter sequence LexAop-Leu2 in place of the chromosomal LEU2, was transformed with pEG202-IL-1-R-1c and pSH18-34 (Ura+), which carries another reporter sequence, LexAop-lacZ. For screening cDNAs encoding proteins that interact with IL-1-R-1c, the expression vector pJG4-5 (TRP1), containing either a WI38 or HeLa cell cDNA library (see below for the cDNA library construction), was transformed into the above strain (EGY48/pEG202-IL-1-R-1c/pSH18-34) according to the method described by Gietz et al., Nucleic Acids Res., 20, 1425, 1992.

The bait used in obtaining clones 14w, 19w and 31w was constructed by cloning the DNA sequences encoding amino acids 477 to 527 of IL-1 receptor p80 into the EcoRI and NotI sites of EG202. The resulting plasmid was named EG202-IL1R (477–527). This region of the IL-1 receptor is believed to be essential for signaling.

cDNA Library Construction:

WI38 cell cDNA library: Double stranded cDNA was prepared from 3 μg of WI38 mRNA using reagents provided by the Superscript Choice System (Gibco/BRL, Gaithersberg, Md.) with the following substitutions: the first strand synthesis was primed using an oligo dT/XhoI primer/linker, and the dNTP mix was substituted with a mix containing methyl dCTP (Stratagene, LaJolla, Calif.). The cDNA was modified at both ends by addition of an EcoRI/NotI/SalI adapter linker and subsequently digested with XhoI. This produced cDNA molecules possessing an EcoRI/NotI/SalI overhang at the 5' end of the gene and an XhoI overhang at the 3' end. These fragments were then ligated into the yeast expression/fusion vector pJG4-5 (Gyuris et al., Cell, 75, 791–803, 1993), which contains at its amino terminus, the influenza virus HA1 epitope tag, the B42 acidic transcription activation domain, and the SV40 nuclear localization signal, all under the control of the galactose-dependent GAL1 promoter. The resulting plasmids were then electroporated into DH10B cells (Gibco/BRL). A total of $7.1 \times 10^6$ colonies were plated on LB plates containing 100 ug/ml of ampicillin. These *E.coli* were scraped, pooled, and a large scale plasmid prep was performed using the Wizard Maxi Prep kit (Promega, Madison, Wis.), yielding 3.2 mg of supercoiled plasmid DNA.

HeLa cell cDNA: HeLa cell cDNA preparation methods are described in Gyuris et al., Cell, 75, 791–803, 1993, which is incorporated herein by reference.

HeLa Cell CDNA Screening Results:

$2 \times 10^5$ transformants were obtained on glucose Ura$^-$His$^-$Trp$^{31}$ plates. These transformants were pooled and resuspended in a solution of 65% glycerol, 10 mM Tris-HCl (pH 7.5), 10 mM MgCl$_2$ and stored at $-80°$ C. in 1mL aliquots. For screening purposes, aliquots of these were diluted 10-fold into Ura$^-$His$^-$Trp$^-$ CM dropout gal/raff medium (containing 2% galactose, 1% raffinose), which induces the expresssion of the library encoded proteins, and incubated at 30° C. for 4 hours. $2 \times 10^6$ colony forming units (CFUs) were then plated on standard 10 cm galactose X-Gal Ura$^-$His$^-$Trp$^-$Leu$^-$ plates at a density of $2 \times 10^5$ CFU/plate. After 4 days at 30° C., colonies that were strong LacZ$^+$ were chosen for further processing. In order to test if the Leu$^+$/LacZ$^+$ phenotype was due to the library-encoded protein, the galactose dependency of the phenotype was tested. Expression of the library-encoded proteins was turned off by growth on glucose Ura$^-$His$^-$Trp$^-$ master plates and then retested for galactose-dependency on glucose Ura$^-$His$^-$Trp$^-$Leu$^-$, galactose Ura$^-$His$^-$Trp$^-$Leu$^-$ glucose X-Gal Ura$^-$His$^-$ Trp$^-$, and galactose X-Gal Ura$^-$His$^-$Trp$^-$ plates. Of these many colonies showed galactose-dependent growth on Leu$^-$ plates and galactose-dependent blue color on X-Gal-containing medium (LacZ$^-$ phenotype). Total yeast DNA was prepared from these colonies according to the method described previously (Hoffman and Winston, 1987). In order to analyze the cDNA sequences. PCR reactions were performed using the above yeast DNA as a template and oligo primers specific for the vector pJG4-5, flanlking the cDNA insertion point. PCR products were purified (Qiagen PCR purification kit), subjected to restriction digest with the enzyme HaeIII run on 1.8% agarose gels, and the restriction patterns compared. Similar and identical restriction patterns were grouped and representatives of each group were sequenced and compared to Genbank and other databases to identify any sequence homologies.

WI38 Cell cDNA Screening Results:

This screen was performed as above with the following exceptions: 1)$1 \times 10^6$ transformants were obtained on glucose Ura$^-$His$^-$Trp$^-$ plates and pooled. 2) $11 \times 10^6$ CFU were screened. Of these, 0.5% were Leu$^+$ and of those, 1% were LacZ$_+$. This gave a frequency of 50 double positives per $10^6$ transformants screened. Colonies, exhibiting a strong LacZ$^+$ phenotype (as judged by the strength of blue color on X-Gal containing medium), were chosen for further processing. Clones with the strongest LacZ+ phenotype were chosen for further specificity tests as described above.

A WI38 cDNA library was transformed into the reporter strain (EGY48/pSH18-34) containing the bait plasmid EG202-IL1R (477–527). 1.3 million primary transformants were harvested and 7 million colonies were screened. 192 galactose-dependent colonies were isolated. Among these, 51 clones were bait specific (i.e., interacted specifically with the original bait, but not with an unrelated bait, bicoid). These clones were then subjected to DNA sequence analysis. Clones 19w was isolated 6, times, clone 31w twice, and clone 14w once.

EXAMPLE 2

EXPRESSION OF THE IL-1-R INTRACELLULAR LIGAND PROTEIN cDNAs encoding IL-1-R intracellular ligand proteins were released from the pJG4-5 vector with the appropriate restriction enzymes. For example, EcoRI and XhoI were used to release cDNA from the relevant clone. Where the restriction sites were also present in the internal sequence of the cDNA, PCR was performed to obtain the cDNA. These cDNAs were then cloned into various expression vectors. These included pGEX (Pharmacia) or pMAL (New England Biolabs) for expression as a GST (Glutathione-S-transferase) or MBP (maltose binding protein) fusion protein in E. coli, a pED-based vector for mammalian expression, and pVL or pBlueBacHis (Invitrogen) for baculovirus/insect expression. For the immunodetection of IL-1-R intracellular ligand expression in mammalian cells, an epitope sequence, "Flag," was inserted into the translational start site of the pED vector, generating the pED-Flag vector. cDNAs were then inserted into the pED-Flag vector. Thus, the expression of cDNA from pED-Flag yields a protein with an amino terminal Met, followed by the "Flag" sequence, Asp-Tyr-Lys-Asp-Asp-Asp-Asp-Lys. Standard DEAE-Dextran or lipofectamine methods were used to transfect COS or CHO dukx cells. Immunodetection of Flag-tagged proteins was achieved using the M2 antibody (Kodak). Moreover, an immunoaffinity column using the M2 antibody, followed by elution with the "Flag" peptide, can be used for the rapid purification of the flag-tagged protein. Similarly, affinity purification of GST-, MBP- or His-tagged fusion proteins can be performed using glutathione, amylose, or nickel columns. Detailed purification protocols are provided by the manufacturers. For many fusion proteins, the IL-1-R intracellular ligand can be released by the action of thrombin, factor Xa, or enterokinase cleavage. In the case where highly purified material is required, standard purification procedures, such as ion-exchange, hydrophobic, and gel filtration chromatography will be applied in addition to the affinity purification step.

FIG. 1 depicts an autoradiograph demonstrating the expression of IL-1-R intracellular ligand proteins in mammalian cells. FIG. 1 shows the results of expression of Flag-14w, -19w and -31w in COS cells. COS cells were transfected with either pED-Flag (vector control), Flag-14w, -19w or -31w plasmid by the lipofectamine method. Thirty $\mu$g of each cell lysate were prepared and subjected to 4–20% SDS gel electrophoresis, followed by Western blot analysis using M2 antibody (Kodak). A Flag-containing protein, Flag-BAP (Kodak), was also loaded as a standard. The bands in the Flag-14w, -19w and -31w indicate significant expression of the respective IL-1-R intracellular ligand proteins.

EXAMPLE 3

ASSAYS OF IL-1-R INTRACELLULAR DOMAIN BINDING

Two different methods were used to assay for IL-1-R intracellular ligand protein activity. The first assay measures binding in the yeast strain in "interaction trap," the system used here to screen for IL-1-R-1c interacting proteins. In this system, the expression of reporter genes from both LexAop-Leu2 and LexAop-LacZ relies on the interaction between the bait protein, in this case IL-1-R-1c, and the prey, the IL-1-R intracellular ligand. Thus, one can measure the strength of the interaction by the level of Leu2 or LacZ expression. The most simple method is to measure the activity of the LacZ encoded protein, β-galactosidase. This activity can be judged by the degree of blueness on the X-Gal containing medium or filter. For the quantitative measurement of β-galactosidase activity, standard assays can be found in "Methods in Yeast Genetics" Cold Spring Harbor, N.Y., 1990 (by Rose, M. D., Winston, F., and Hieter, P.).

The second assay for measuring binding is a cell-free system. An example of a typical assay is described below. Purified MBP-IL-1-R-1c fusion protein (2 $\mu$g) was mixed with glutathione-Sepharose 4 B beads bound with a GST-IL-1-R-1c intracellular ligand for 2 hour at 4° C. The mixture was then centrifuged to separate bound (remained with the beads) and unbound (remained in the supernatant) MBP-IL-1-R-1c. After extensive washing, the bound MBP-IL-1-R-1c was eluted with glutathione and detected by Western blot analysis using an MBP antibody. The IL-1-R-1c or the intracellular ligand can also be immobilized on other solid supports, such as on plates or fluorobeads. The binding can then be measured using ELISA or SPA (scintillation proximity assay).

EXAMPLE 4

CHARACTERIZATION OF IL-1-R INTRACELLULAR LIGAND PROTEIN

Mapping the interaction site in IL-1-R-1c

Many of the key amino acids for IL-1-R signaling have been determined by site-directed mutagenesis (Heguy et al., 1992, JBC, 267, 2605–2609). These amino acids are conserved between IL-1-R and the Drosophila Toll protein, which is required for transducing dorsoventral positional information to cells in the developing embryo. In order to test if the IL-1-R intracellular proteins interact with these residues, these residues were mutagenized and the ability of the mutant protein to interact with the intracellular ligand in the "interaction trap" system was tested. Mutations that abolish IL-1R signaling were introduced into the original bait plasmid, EG202-IL-1R (477–527) (with-following amino acid substitutions: F513A, W514A, K515R, R518K, and Y519S) and the ability of the IL-1R intracellular ligands to interact with these mutant proteins was tested in the interaction trap. EGY48 carrying pSH18-34 (lexAop-LacZ) were cotransformed with two plasmids: one carrying 14w, 19w or 31w; the other with bait, EG202-IL1R (477–527), either wild-type or one of the mutants. transformants were then streaked onto CM ura⁻his⁻trp⁻ plates containing galactose/raffinose and β-gal. The strength of interaction (as indicated by the number of "+" signs) was judged by the blueness in the plates (indicator of LacZ expression). The results are summarized in Table I.

TABLE I

| bait → clone ↓ | WT | F513A | W514A | K515R | R518K | Y519S |
|---|---|---|---|---|---|---|
| 14w | +++ | ++ | + | +++ | +++ | + |
| 19w | + | − | + | ++ | − | − |
| 31w | ++ | − | − | +++ | − | − |

Clone 14w interacted with mutant baits W514A and Y519S much more weakly than with wild-type bait. Clone 19w interacted differentially with wild-type and manu of the mutant baits. It appeared to interact with the mutant bait K515R more strongly than with wild-type, while reduced interaction was observed with mutant baits F513R, R518K and Y519S. The interaction of clone 31w was significantly reduced by mutations F513A, W514A, R518K and Y519S. The change in the interaction strength by these mutations suggests that these residues are the site(s) of interaction. therefore, these data suggest that clones 14w, 19w and 31w interact with many of the signaling residues and may play a role in IL-1R signaling.

Effect on the IL-1-mediated response

The effect of the IL-1-R intracellular ligands on the IL-1-mediated response can be evaluated in cells overexpressing the ligands. A number of IL-1 mediated responses, including transient or prolonged responses, can be measured. For example, IL-1-induced kinase activity toward either MBP (myelin basic protein) or the N-terminus (amino acids 1–79) of c-jun can be measured in COS cells or CHO cells either transiently or stably overexpressing IL-1R intracellular ligand proteins. Alternatively, other functional assays, such as the induction of gene expression or $PGE_2$ production after prolonged incubation with IL-1, can also be used to measure the IL-1 mediated response. Conversely, the significance of the IL-1-R intracellular ligand proteins in IL-1signaling can be established by lowering or eliminating the expression of the ligands. These experiments can be performed using antisense expression or transgenic mice.

IL-1 mediated JNK (c-jun $NH_2$-terminal kinase, Derjard et al., Cell 1994, 76, 1025–1037) activation was used to study the effect of the IL-1R intracellular ligands on IL-1 signaling. COS cells were transfected with both pEDflag plasmid containing one of the clones (e.g., 19w) and HA-JNK1 plasmid by the DEAE-dextran method. 48 hrs after transfection, cells were starved in 0.1% BSA for 1 hr and treated with various amounts of IL-1α for 15 min. Cells were then lysed, centrifuged and immunoprecipitated with anti-HA monoclonal antibody, 12CA5 (Boehringer Mannheim). JNK activity was performed at 30° C. for 20 min using 5 μg GST-c-jun (1–79 amino acids), 20 μM ATP, and 5 μCi [γ-$^{32}$P]ATP in 40 μl of kinase buffer (25 mM HEPES, pH 7.5, 20 mM $MgCl_2$, 20 mM μ-glycerophosphate, 0.1 mM sodium orthovanadate, 2 mM DTT). The reactions were terminated using laemmli sample buffer and the products were resolved by SDS-PAGE (4–20%).

Figure 2A:
FIG. 2 demonstrates the effects of the clone 19w product on JNK1 activation. Top panel: HA-tagged JNK1 was coexpressed in COS cells with either pED flag vector of pED flag-19w. After 48 hr, the cells were treated with different concentrations of IL-1α for 15 min. JNK1 was isolated by immunoprecipitation with 12CA5 antibody and JNK activity was measured using an immune complex kinase assay with the substrate GST-c-jun (1–79). Middle panel: The expression and recovery if HA-JNK1 from immunoprecipitation was examined by Western blot analysis wit 12CA5 antibody. Bottom panel: The expression of clone 19w was detected by Western blot analysis of cell lysate using M2 antibody.
Figure 2B:
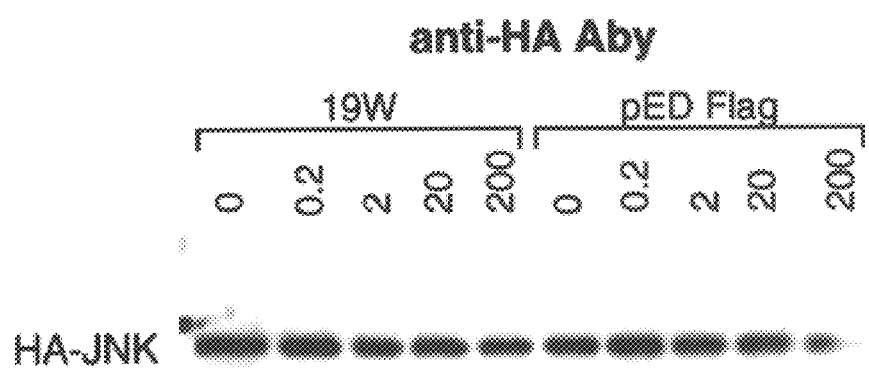
Figure 2C:
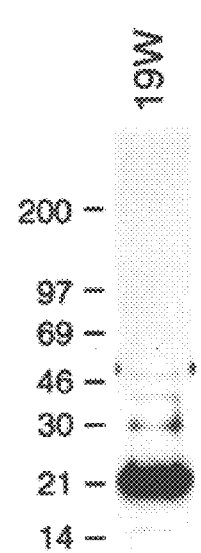

As shown in FIG. 2, expression of clone 19w stimulated JNK activity in all IL-1 concentrations tested as compared to the pED flag vector transfected cells. It also enhanced JNK activity even in the absence of IL-1. These data strongly suggest that clone 19w, through its interaction with the signaling domain of IL-1 receptor (i.e., amino acids 477–527 of IL-1R), may indeed participate in the signaling event.

Enzymatic or functional assays

The signal transduction events initiated by IL-1 binding to its receptor are still largely unknown. However, one major result of IL-1 binding is the stimulation of cellular serine/threonine kinase activity. In addition, IL-1 has been shown to stimulate the activity of PC-PLC, $PLA_2$, and sphingomyelinase. Therefore, some of the IL-1-R intracellular ligand proteins may possess intrinsic enzymatic activity that is responsible for these activities. Therefore, enzymatic assays can be performed to test this possibility, particularly with those clones that encode proteins with sequence homology to known enzymes. In addition to enzymatic activity, based o n the sequence homology to proteins w it h known function, other functional assays, for instance, ATP binding/transporter activity for the full length protein of clone 140, can also be measured.

EXAMPLE 5

ISOLATION OF FULL LENGTH CLONES

In many cases, cDNAs obtained from the interaction trap method each encode only a portion of the full length protein. Therefore, it is desirable to isolate full length clones. The cDNAs obtained from the screening are used as probes, and the cDNA libraries described herein, or alternatively phage cDNA libraries, are screened to obtain full length clones in accordance with known methods (see for example, "Molecular Cloning, A Laboratory Manual", by Sambrook et al., 1989 Cold Spring Harbor).

EXAMPLE 6

ANTIBODIES SPECIFIC FOR IL-1-R INTRACELLULAR LIGAND PROTEIN

Antibodies specific for IL-1-R intracellular ligand proteins can be produced using purified recombinant protein, as described in Example 2, as antigen. Both polyclonal and monoclonal antibodies will be produced using standard techniques, such as those described in "Antibodies, a Laboratory Manual" by Ed Harlow and David Lane (1988), Cold Spring, Harbor Laboratory.

What is claimed is:

1. An isolated protein having IL-1-R intracellular ligand protein activity and comprising the amino acid sequence of SEQ ID NO:2 said protein being substantially free from other mammalian proteins.

2. A composition comprising the protein of claim 1 and a pharmaceutically acceptable carrier.

3. An isolated protein having IL-1-R intracellular ligand protein activity and comprising the amino acid sequence of SEQ ID NO:4 said protein being substantially free from other mammalian proteins.

4. A composition comprising the protein of claim 3 and a pharmaceutically acceptable carrier.

5. An IL-1-R intracellular ligand protein produced according to a method comprising:
   (1) growing a culture of a host cell transformed with a polynucleotide which is operably linked to an expression control sequence in a suitable culture medium; and
   (2) purifying said IL-1-R intracellular ligand protein from the culture wherein said polynucleotide encodes a protein having IL-1-R intracellular ligand protein activiy, and wherein said polynucleotide is selected from the group consisting of:
      (a) a polynucleotide comprising the nucleotide sequence of SEQ ID NO:1 from nucleotide 2 to nucleotide 529; and
      (b) a polynucleotide encoding an IL-1-R intracellular ligand protein comprising the amino acid sequence of SEQ ID NO:2.

6. A composition comprising the protein of claim 5 and a pharmaceutically acceptable carrier.

7. The protein of claim 5, wherein said polynucleotide comprises the nucleotide sequence of SEQ ID NO:1 from nucleotide 2 to nucleotide 529.

8. The protein of claim 5, wherein said polynucleotide comprises a polynucleotide encoding a protein comprising the amino acid sequence of SEQ ID NO:2.

9. An IL-1-R intracellular ligand protein produced according to a method comprising:
   (1) growing a culture of a host cell transformed with a polynucleotide which is operably linked to an expression control sequence in a suitable culture medium; and
   (2) purifying said IL-1-R intracellular ligand protein from the culture wherein said polynucleotide encodes a protein having IL-1-R intracellular ligand protein activity, and wherein said polynucleotide is selected from the group consisting of:
      (a) a polynucleotide comprising the nucleotide sequence of SEQ ID NO:3 from nucleotide 2 to nucleotide 961; and
      (b) a polynucleotide encoding an L-1-R intracellular ligand protein comprising the amino acid sequence of SEQ ID NO:4.

10. A composition comprising the protein of claim 9 and a pharmaceutically acceptable carrier.

11. The protein of claim 9, wherein said polynucleotide comprises the nucleotide sequence of SEQ ID NO:3 from nucleotide 2 to nucleotide 961.

12. The protein of claim 9, wherein said polynucleotide comprises a polynucleotide encoding a protein comprising the amino acid sequence of SEQ ID NO:4.

* * * * *